(12) United States Patent
Ishida

(10) Patent No.: US 6,184,977 B1
(45) Date of Patent: Feb. 6, 2001

(54) INSPECTION METHOD AND INSPECTION DEVICE

(75) Inventor: Futoshi Ishida, Takatsuki (JP)

(73) Assignee: Minolta Co., Ltd., Osaka (JP)

( * ) Notice: Under 35 U.S.C. 154(b), the term of this patent shall be extended for 0 days.

(21) Appl. No.: 09/280,990

(22) Filed: Mar. 30, 1999

(30) Foreign Application Priority Data

Mar. 30, 1998 (JP) .................................................. 10-083464

(51) Int. Cl.[7] .................................................. G01N 21/88
(52) U.S. Cl. .................................... 356/239.1; 356/239.2
(58) Field of Search ........................ 356/239.1, 239.2, 356/239.3, 239.7

(56) References Cited

U.S. PATENT DOCUMENTS

| 3,202,043 | * | 8/1965 | Galey et al. ......................... 356/239 |
| 4,456,375 | * | 6/1984 | Gardiner et al. ..................... 356/239 |
| 4,989,973 | * | 2/1991 | Noso et al. .......................... 356/239 |
| 5,726,749 | * | 3/1998 | Schave ................................. 356/239 |

FOREIGN PATENT DOCUMENTS

| 05119468 | 5/1993 | (JP) . |
| 06258236 | 9/1994 | (JP) . |
| 07225198 | 8/1995 | (JP) . |
| 08201313 | 8/1996 | (JP) . |

* cited by examiner

*Primary Examiner*—Richard A. Rosenberger
(74) *Attorney, Agent, or Firm*—McDermott, Will & Emery

(57) ABSTRACT

An method and device for inspecting for surface defects, internal defects, and surface-adhered foreign matter on semitransparent materials. An illuminating device transmits light, that is then collimated through a collimating lens unit, through an object to be inspected. The light then transmits through the object to be inspected an eventually is detected by a detector. Any defects in the object to be inspected will be detected.

7 Claims, 4 Drawing Sheets

| Precision Rank | Kind of Defect and Inspectable Size | | |
|---|---|---|---|
| | (Pit) | (Particle) | (Scratch) |
| A | 3 μm less than | 3 μm less than | 2 μm less than |
| B | 2 ~ 5 μm | 2 ~ 5 μm | 1 ~ 4 μm |
| C | 5 ~ 10 μm | 5 ~ 10 μm | 3 ~ 10 μm |
| D | 10 ~ 20 μm | 10 ~ 20 μm | 10 ~ 20 μm |
| E | 20 μm over | 20 μm over | 20 μm over |

(Scratch: Wide, Other: Diameter)

FIG. 8

INSPECTION METHOD AND INSPECTION DEVICE

CROSS-REFERENCED APPLICATIONS

This application is based on Application No. HEI 10-83464 filed in Japan, the content of which is hereby incorporated by reference.

BACKGROUND OF THE INVENTION

1. Field of the Invention

The present invention relates to a method and device for inspecting for surface defects, internal defects, and surface-adhered foreign matter on semitransparent materials. Specifically, the present invention relates to a method and device for inspecting for surface defects, internal defects, and surface-adhered foreign matter on semitransparent hard disk substrates, liquid crystal display panels, lenses and the like.

2. Description of the Related Art

In general, inspection methods and inspection devices for detecting surface defects (scratches, pits), internal defects (air bubbles, contaminants), surface-adhered foreign matter (adhered small particles) (hereinafter referred to collectively as "defects") and the like in hard disk substrates, liquid crystal display panels, lenses and the like formed of semitransparent material can be separated into: inspection methods and inspection devices of the reflection type, which inspect for defects from information included in light reflected by the surface of the object being inspected (hereinafter referred to as "inspection object"); and inspection methods and inspection devices of the transmission type, which inspect for defects from information included in light transmitted through the inspection object.

In inspection methods and inspection devices of the reflection type, disadvantages arise in that the inadequate contrast between the scattered light from a defect area and the reflected light from the non-defect area due to low light reflectivity of the transparent or semitransparent inspection object prevents satisfactory defect inspection from being attained. Furthermore, the reflected light from the inspection object includes not only reflected light from the surface of the inspection object on the light source side (surface reflected light), but also includes reflected light from the surface of the inspection object on the side opposite the light source (back surface reflected light), which presents the disadvantage of eliminating the effects of this back surface reflected light from the inspection results.

In inspection methods and inspection devices of the transmission-type, on the other hand, while they do not have the disadvantages typical of the inspection methods and devices of the reflection type, they are subject to dispersion of the scattered light in all directions because they use a construction which condenses (collects) the light from a light source at the inspection position of the inspection object, i.e., they use a construction which causes light to enter the inspection position from various angles. This type of construction is disadvantageous in that there is insufficient contrast between the scattered light from a defect area and the transmitted light from the non-defect area, such that defect inspection cannot be readily accomplished.

SUMMARY OF THE INVENTION

An object of the present invention is to provide a novel inspection method and inspection device capable of easily detecting defects in an inspection object formed of transparent or semitransparent material.

The present invention utilizes substantially parallel light rays to illuminate an inspection object in a detection method for detecting defects of an inspection object from illumination light transmitted through a detection object formed of transparent or semitransparent material. This substantially parallel light includes not only completely parallel light but also light which can be regarded as completely parallel.

Other modes of the inspection method of the present invention observe the inspection object from a direction substantially parallel to the direction of advancement of the substantially parallel light.

The inspection device of the present invention embodies the inspection method of the invention, and utilizes substantially parallel light rays to illuminate an inspection object in a detection method for detecting defects of an inspection object from illumination light output from a light source and transmitted through a detection object formed of transparent or semitransparent material.

Another mode of the inspection device of the present invention sets the light source and inspection object to a relationship such that the light output from a light source becomes substantially parallel at the position of the inspection object in a detection device for detecting defects of an inspection object from illumination light emitted from a light source and transmitted through a detection object formed of transparent or semitransparent material.

Another mode of the inspection device of the present invention provides a detection unit for detecting defects of an inspection object such that the inspection object is observed from a direction substantially parallel to the direction of advancement of the substantially parallel light.

Another mode of the inspection device of the present invention provides a detection unit for detecting defects of an inspection object, said detection unit being disposed at a position such that the light transmitted through the inspection object does not directly enter.

Yet another mode of the inspection device of the present invention provides a light shield member between a light source and an inspection object or between an inspection object and the detection unit such that light transmitted through an inspection object to the detection unit for detecting defects of the inspection object does not directly enter.

Still another mode of the inspection device of the present invention moves light shield member relative to the inspection object.

These and other objects, advantages and features of the invention will become apparent from the following description thereof taken in conjunction with the accompanying drawings which illustrate specific embodiments of the invention.

BRIEF DESCRIPTION OF THE DRAWINGS

In the following description, like parts are designated by like reference numbers throughout the several drawings.

FIG. 8 is a table showing precision ranking of types of defects.

DESCRIPTION OF THE PREFERRED EMBODIMENTS

Figure 1:
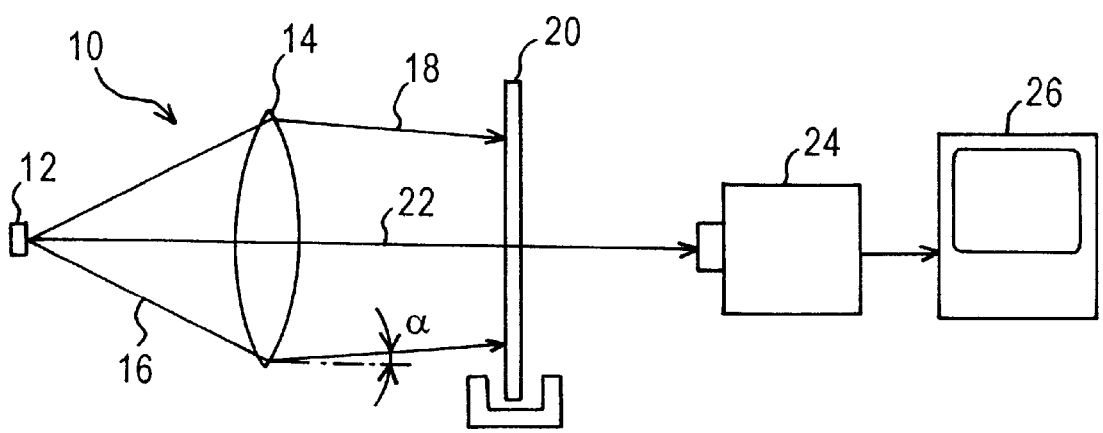
FIG. 1 is a side view briefly showing the construction of a first inspection device of the present invention.

FIG. 1 briefly shows the construction of a first inspection device of the present invention. A device 10 (inspection device) for detecting defects in an inspection object is provided with a light source 12. The light source 12 is provided with a halogen lamp and a light guide (neither is shown in the drawing), and guides the light emitted from the halogen lamp to a first collimating lens unit 14 via the light guide. The collimating lens unit 14 is provided with a single lens or a plurality of lenses to collimate the light 16 emitted from the light source 12 into substantially parallel light 18 to illuminate an inspection object 20. In the present embodiment, the inspection object 20 is a panel formed of transparent or semitransparent material held by holder 25 in a direction perpendicular to the optical axis of the collimating lens unit 14. A detection device (CCD camera) 24 for detecting defects is arranged on the opposite side of the collimating lens unit 14 to sandwich the inspection object 20 therebetween and positioned such that the optical axis of the detection device 24 matches the optical axis 22 of the collimating lens unit 14 so as to capture the light transmitted through the inspection object 20. The detection device 24 is connected to a display device (monitor) 26, such that an image of the inspection object 20 projected by the detection device 24 is displayed on the display device 26. A second lens unit may be provided between the inspection object 20 and the detection device 24 to condense the light transmitted through the inspection object 20 on the detection device 24.

According to the inspection device 10, the light 16 emitted from the light source 12 is converted to substantially parallel light 18 by the collimating lens unit 14, and illuminates the inspection object 20. The detection device 24 captures the light transmitted through the inspection object 20, and an image formed by this light is displayed on the display device 26.

Figure 2:
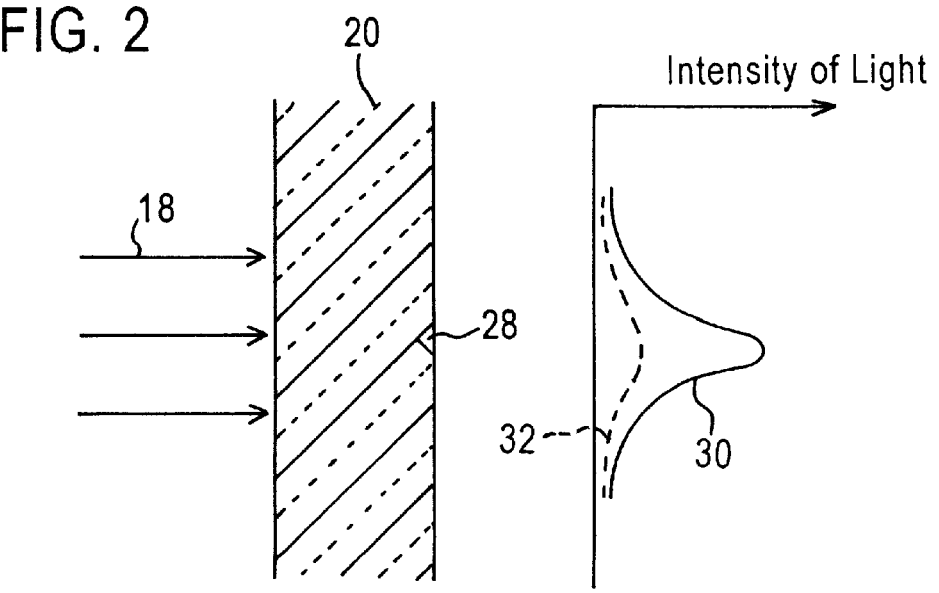
FIG. 2 is an intensity distribution diagram of the light transmitted through an inspection object.

The image projected on the display device 26 is described below with reference to FIG. 2. When there is no defect 28 present in the inspection object 20, the image projected on the display device 26 has a uniform light intensity. When a defect 28 is present in the inspection object 20, the angle of the light flux impinging the defect 28 becomes near identical due to the illumination by the substantially parallel light, and the scattering direction is uniform. In this way, the image projected on the display device 26 has locally increased light intensity of the scattered light corresponding to the defect 28 (refer to solid line 30 in the drawing) For reference, the curve 32 depicted by the dashed line in FIG. 2 represents the light intensity distribution appearing on the display device corresponding to the scattered light of the defect when the light from the light source is condensed at the inspection position of the lens unit as described in the section on the conventional art, and although the intensity of the scattered light increases somewhat, this increase is not necessarily of a level sufficient to be recognized. For this reason, the inspection device 10, which illuminates an inspection object with substantially parallel light, is capable of more easily inspecting defects than is a conventional inspection device. When the region that can be illuminated by the light source 12 and the collimating lens unit 14 is limited to one part of the inspection object 20, defect inspection can be accomplished on the entire surface of the inspection object 20 while moving the inspection object 20 within a plane perpendicular to the optical axis. When the inspection object is relatively small, however, the inspection can be accomplished without moving the inspection object in a direction perpendicular to the optical axis because virtually the entire surface of the inspection object can be illuminated by using a lens having a diameter equal to the inspection object.

An example of defect inspection using the inspection device 10 is described below. The inspection conditions are as follows.

(1) The light source used a halogen lamp and a light guide to direct the emitted light. The aperture of the emission end of the light guide was set at a diameter of 4 mm. The luminance of the light impinging the inspection object was 150 lux.

(2) A single condensing lens was used as the first lens unit. This condensing lens has an aperture of a diameter of 50 mm, and focal length of 80 mm. The distance between the inspection object and the condensing lens was set at 300 mm, and the illumination aperture on the inspection object was adjusted to a diameter of 40 mm (the angle α formed between the optical axis and the light transmitted through the outermost edge of the lens is about 1 degree).

(3) A 0.5× magnification lens unit was used as the second lens unit disposed between the inspection object and the detection device.

(4) A CCD camera (½ inch, 410,000 pixel) was used as the detection device.

(5) A glass plate (thickness: 1 mm) was used as the inspection object.

As a result of the defect inspection, surface pits and particles on the order of 3 microns, and surface scratches on the order of 2 microns in width were detected.

Although it is desirable that the light impinging the inspection object is entirely parallel light, the objects of the present invention can be attained insofar as this light is substantially parallel. It has been determined experimentally by the present inventors that defect inspection precision changes by the angle α formed between the optical axis and the light transmitted through the outermost edge of the lens to the inspection object in the first lens unit according to the conditions described below. Defect inspection precision was evaluated according to the ranking shown in the Table of FIG. 8.

Experimental results show that a precision rank of B was obtained when the angle α is less than 10 degrees, and a precision rank of C was obtained when the angle α is 10 degrees or greater. A precision rank of A was obtained when the angle α was less than 5 degrees.

When the size of the light source is increased, the conditions are lost for converting the light emitted from the light source at various points into substantially parallel light which impinges the inspection object from various different angle. Accordingly, a small light source is desirable (aperture of less than a diameter of 8 mm). A light source of a certain size is necessary to ensure the amount of light reaching the detection device. In ensuring as far as possible the amount of light necessary, the light source may be a pinhole light source, and in this instance the substantially parallel light can be directed to impinge the inspection object by adjusting the distance between the light source, the first lens unit, and the inspection object. Furthermore, the impingement on the inspection object may be adjusted by providing a pinhole, aperture or the like in the first lens unit. If a pinhole or the like is used to materially reduce the size of the light source, the conditions for the producing the substantially parallel light are mitigated due to the adverse affects of light emitted from the light source at various points impinging the defect area at different angles. When a pinhole of a diameter of 100 µm is used, the angle α exceeds 10 degrees, and an inspection precision rank of C is obtained.

Figure 3:
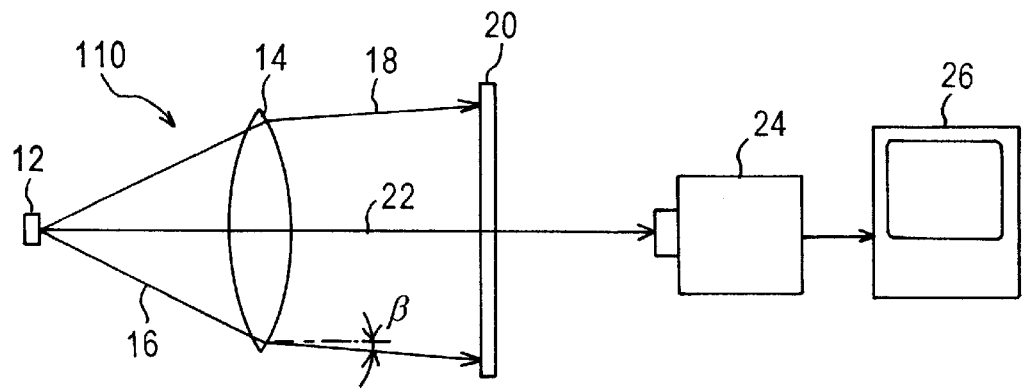
FIG. 3 is a side view briefly showing the construction of a second inspection device of the present invention.

FIG. 3 shows an inspection device 110 of a second embodiment. This inspection device 110 is constructed so that light transmitted through the collimating lens unit 14 is somewhat diffused to illuminate an inspection object. The inspection device 110 is advantageous in that a region the size of the inspection object 20 can be illuminated. The angle β formed between the optical axis and the light transmitted through the outermost edge of the lens is desirably less than 10 degrees, and more desirably less than 5 degrees.

Defects in the inspection object 20 were detected using the inspection device 110. The inspection conditions were identical to the conditions for the inspection device 10 with the exception that the illumination aperture on the inspection object 20 was set at a diameter of 60 mm (the angle β formed between the optical axis and the light transmitted through the outermost edge of the lens was approximately 1 degree). The inspection results are shown in the Table of FIG. 8; an inspection precision of rank A was obtained.

Figure 4:
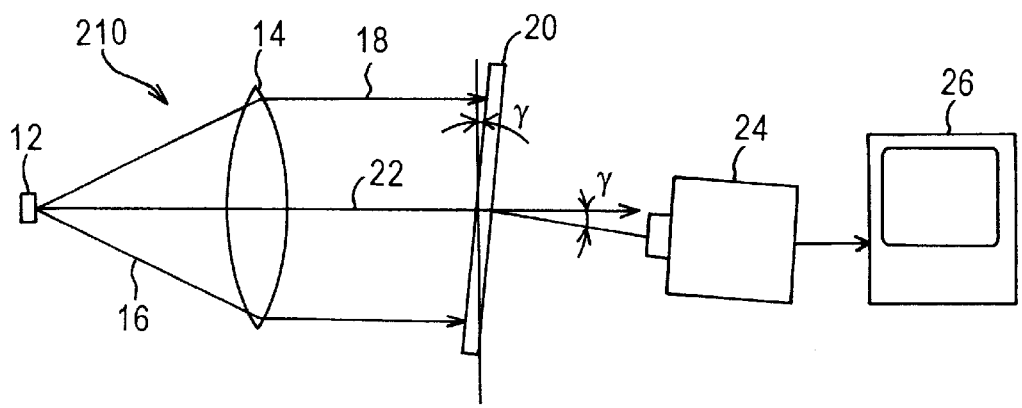
FIG. 4 is a side views briefly showing the construction of a third inspection device of the present invention.

FIG. 4 shows an inspection device 210 of a third embodiment. In the inspection device 210, the inspection object 20 is inclined at a predetermined angle γ relative to a plane intersecting the optical axis 22 of the collimating lens unit 14. The detection device 24 is positioned with its optical axis set at an angle perpendicular to the inspection object 20. Defect inspection was conducted using the inspection device 210 under the same conditions as used with the inspection device 10, and with the angle γ set at 1 degree. Inspection precision of rank A shown in the Table of FIG. 8 was obtained as a result. The inspection device 210 increases the brightness of the light source 12 so as to increase the intensity of the scattered light of the defect area output to the display device and increase the contrast and the intensity of the light transmitted through the non-defect area, and thereby improving the defect inspection precision over the other embodiments by preventing light from the light source 12 from directly entering the detection device 24.

The inclination angle γ between the inspection object 20 and the detection device 24 is desirably less than 10 degree, and more desirably less than 5 degrees. The light source 12 and the detection device 24 may be moved parallel to a direction perpendicular to their respective optical axes. The detection device 24 may be provided outside the extended region of the substantially parallel light 18 so as to not have light emitted from the light source 12 enter the detection device 24.

The holder 25 adjustably holds the inspection object 20 at any one position in a range of positions ranging from a position perpendicular to the optical axis of the collimating lens unit 14, such as depicted in FIG. 1, to a position inclined at a predetermined angel relative to a plane perpendicularly intersecting the optical axis of the collimating lens unit 14, such as depicted in FIG. 4. The controlling device (not shown) would enable the operator to choose the angle for which the holder 25 would hold the inspection object 20.

Figure 5:
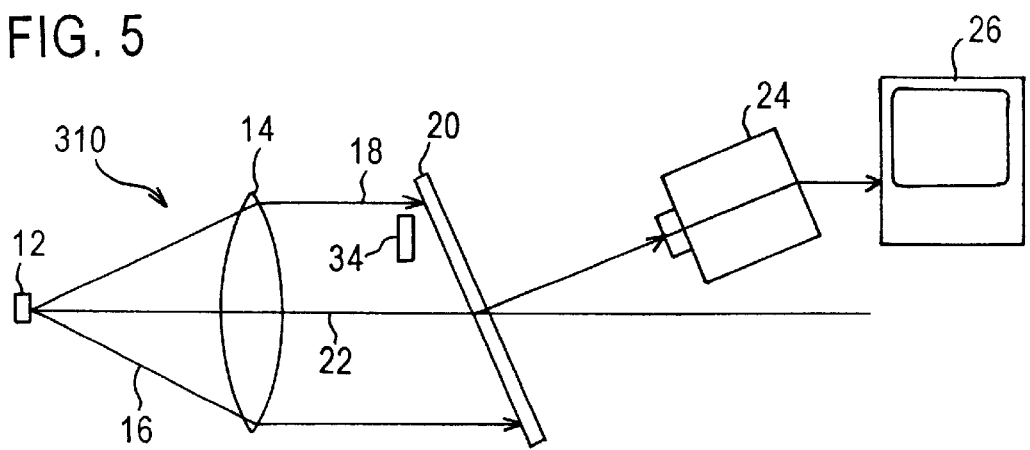
FIG. 5 is a side view briefly showing the construction of a fourth inspection device of the present invention.

FIG. 5 shows an inspection device 310 of a fourth embodiment. In the inspection device 310, a light shield member 34 is provided in part of the optical path between the inspection object 20 and the lens unit 14 of the inspection object 20, such that light transmitted through the inspection object 20 does not directly enter the detection device 24. Various materials may be used for the light shield member 34 insofar as the member does not transmit light, e.g., a black color metal plate, or plastic plate may be used. The inspection device 310 increases the brightness of the light source 12 so as to increase the intensity of the scattered light of the defect area output to the display device and increase the contrast and the intensity of the light transmitted through the non-defect area, and thereby improving the defect inspection precision over the other embodiments by preventing light from the light source 12 from directly entering the detection device 24.

Figure 6:
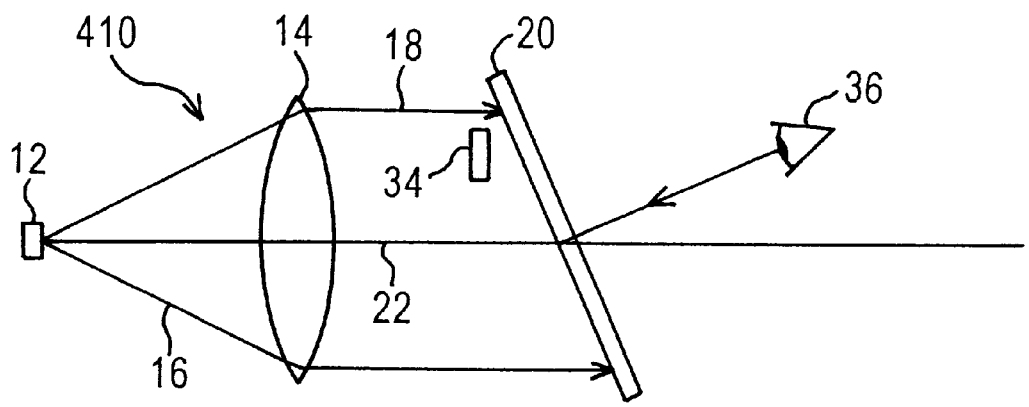
FIG. 6 is a side view briefly showing the construction of a fifth inspection device of the present invention.

FIG. 6 shows an inspection device 410 of a fifth embodiment. In this inspection device 410, an observer 36 visually detects defects instead of the detection device. In this embodiment in particular, it is desirable to provide a light shield member in part of the optical path between the inspection object 20 and the lens unit 14 of the inspection object 20 so as to prevent light transmitted through the inspection object 20 from directly entering the eye of the observer 36. When this light shield member 34 is provided, eye fatigue of the observer 36 is reduced to provide greater inspection precision. When the light shield member 34 was omitted and visual inspection performed, the light of the light source 12 became blinding and an inspection precision rank of D was obtained whereas an inspection precision rank of A was obtained when the light shield member 34 was provided.

Figure 7:
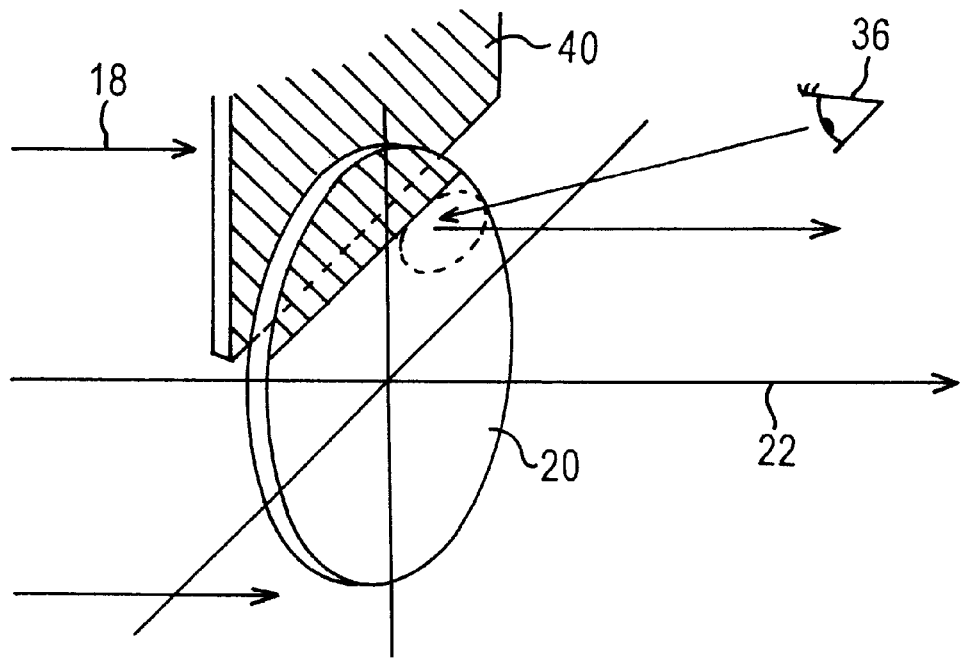
FIG. 7 is a perspective view of an inspection device using a large panel as a light shield member.

The size of the light shield member 34 is not limited, inasmuch as a larger light shield member 40 shown in FIG. 7 may be used to cover the top half, bottom half, right half, or left half of the inspection object 20. Alternatively, a shield panel open only at an observation area may be used. In this instance, the entire surface of the inspection object 20 may be inspected for defects by the observer 36 moving the line of sight or moving the eye position, or by moving the relative positions of the inspection object and the light shield member 40 while maintaining the eye at a constant position.

The embodiments described above are nothing more than specific examples of the present invention and may be variously modified in accordance with inspection conditions. For example, a slit light source may be used as a light source, and a cylindrical lens may be used as the first lens unit so as to illuminate the inspection object with a band like illumination. This modification is particularly effective when performing defect inspections visually, and is advantageous in that defects can be easily confirmed within the band-like transmission like.

Furthermore, it is desirable that the second lens element provided on the side opposite the first lens unit so as to sandwich the inspection object therebetween is a magnification projection optical system to allow inspection of minute defects. A laser may also be used as the light source.

What is claimed is:

1. An inspection device comprising:
    a light source;
    a collimating lens unit which collimates light emitted from said light source into substantially parallel light;
    a holder which holds an inspection object in the path of said collimated light; and
    a detector disposed in the path of light through said inpsection object to detect light transmitted through the inspection object; and
    a light shield member residing in a first portion of the optical path between the inspection object and the collimating lens unit, wherein the light in the remaining portion of the optical path transmitted through the inspection object does not directly enter the detector if the inspection object has no optical defects in such remaining portion of the optical path.

2. The inspection device according to claim 1, wherein said holder holds the inspection object inclined at a predetermined angle relative to a plane perpendicularly intersecting the optical axis of said collimating lens unit and said detector is arranged with its optical axis set at an angle perpendicular to the inspection object.

3. The inspection device according to claim 1, wherein said holder holds the inspection object perpendicular to the optical axis of said collimating lens unit.

4. The inspection device according to claim 1, wherein said holder adjustably holds the inspection object at any position in a range of positions ranging from a position perpendicular to the optical axis of said collimating lens unit to a position inclined at a predetermined angle relative to a plane perpendicularly intersecting the optical axis of said collimating lens unit.

5. The inspection device according to claim 1, wherein an angle formed between the optical axis of said collimating lens unit and the light transmitted through the outermost edge of said collimating lens unit is less than 10 degrees.

6. The inspection device according to claim 1, wherein an angle formed between the optical axis of said collimating lens unit and the light transmitted through the outermost edge of said collimating lens unit is less than 10 degrees.

7. The inspection device according to claim 1, further comprising:

a detector disposed outside the path of the parallel light from said collimating lens unit.

* * * * *